United States Patent
Su

(10) Patent No.: US 6,474,157 B2
(45) Date of Patent: Nov. 5, 2002

(54) SONIC LEVEL MEASURING METHOD

(75) Inventor: Tyan Khak Su, Ottawa (CA)

(73) Assignees: International Hydrosonic Co., Ltd., Seoul (KR); Hydrosonic International Co., Ltd., Ottawa (CA)

( * ) Notice: Subject to any disclaimer, the term of this patent is extended or adjusted under 35 U.S.C. 154(b) by 10 days.

(21) Appl. No.: 09/752,451

(22) Filed: Jan. 3, 2001

(65) Prior Publication Data

US 2002/0050166 A1 May 2, 2002

(30) Foreign Application Priority Data

Sep. 15, 2000 (KR) .................................. 2000-54332

(51) Int. Cl.[7] ........................... G01F 23/28; G01F 23/00
(52) U.S. Cl. ........................................ 73/290; 73/290 R
(58) Field of Search ........................ 73/290 R, 290 V

(56) References Cited

U.S. PATENT DOCUMENTS 5,842,374 A  * 12/1998 Chang ...................... 73/290 R

FOREIGN PATENT DOCUMENTS

DE          19511234          12/1995

* cited by examiner

Primary Examiner—Hezron Williams
Assistant Examiner—Rodney Frank
(74) Attorney, Agent, or Firm—Lee & Sterba, P.C.

(57) ABSTRACT

A sonic level measuring method comprises steps of disposing N sonic receivers $5_1, 5_2, 5_3, \ldots 5_n$ at a constant interval l toward a water surface along the longitudinal portion of a waveguide tube, oscillating sonic pulses to detect the number $N_i$ of the sonic receivers and computing an interval $L_i = (N_i - 1) l$ between a sonic receiver $5_i$ that is positioned on the original point for the water level measurement, measuring a transit time $$t_1 = \frac{l}{C}$$

that it takes for the sonic pulse to be transited between a sonic receiver $5_{i-1}$ and the sonic receiver $5_i$, measuring a transit time $$t_2 = \frac{2\Delta L}{C}$$

from the receiving moment of the advancing sonic pulse until the sonic pulses are reflected on the water surface and then again received by the sonic receiver $5_i$, computing an interval $\Delta L$ between the sonic receiver $5_i$ and the water surface, adding the interval $\Delta L$ to $L_i$ and obtaining a distance $Lx = L_i + \Delta L$ thereby to measure the water level.

2 Claims, 3 Drawing Sheets

FIG. 1
(PRIOR ART)
FIG. 2
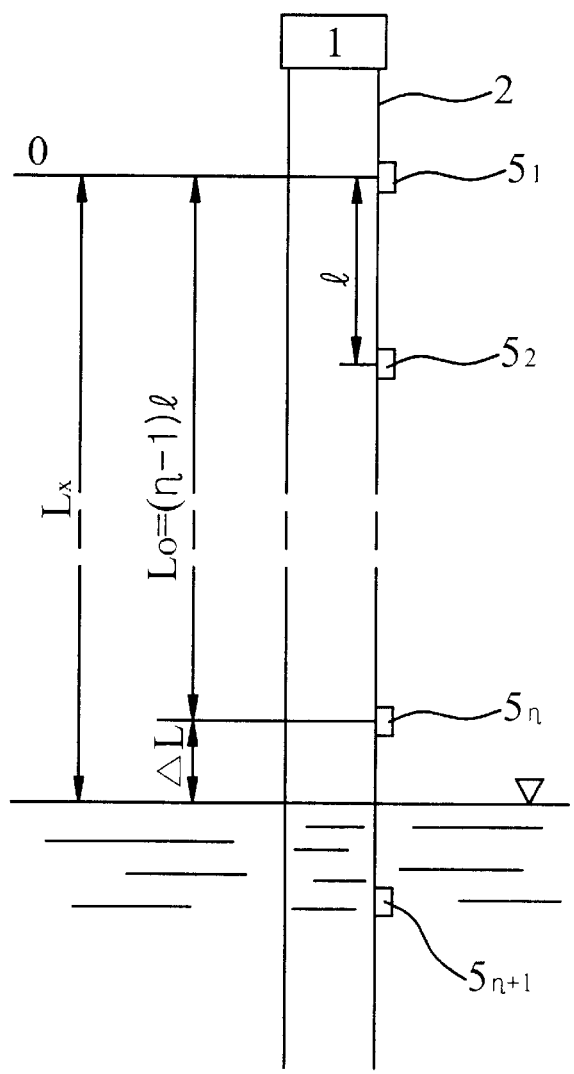
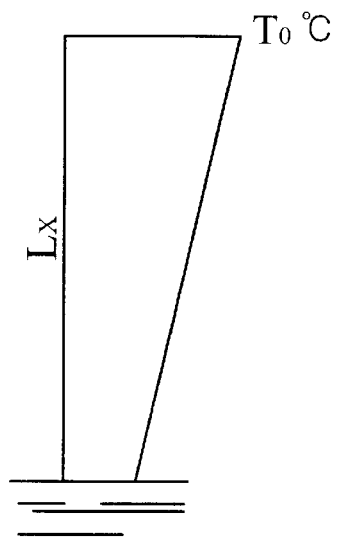

SONIC LEVEL MEASURING METHOD

BACKGROUND OF THE INVENTION

The invention is related to a sonic level measuring technology, and particularly, to a sonic level measuring method of measuring a water level in a high accuracy using a sonic wave in a reservoir, a river, underground water or subterranean, etc. a water level range of which is highly changed.

PRIOR ART

A changing range of a water level in an artificial reservoir is a few tens of meters. There are many rivers that have a water level changing range of 10 m. It is requested for the hydrology observation so that an absolute error of a water level measurement is below ±5~10 m independent of a water level changing range. An original point of a level meter is often placed at a higher position over a water surface according to the mounting condition of the level meter. In this case, even through the changing range of the water level is small, the water measuring range may become greater. In this case, a distance from the original point of the water level to a water surface is normally 10 to 20 m. If the water level change is the range of ±5 m, the water level measuring range becomes 10 to 15 m or 15 to 25 m. In case that a level meter is mounted on a dam in a reservoir, a water level measuring range normally becomes 40 to 80 m. Further, when it is intended to measure a level of the underground water, even though the underground water level is not changed at a high range, the water level is measured by the reference of an original point constituted as a top of an underground water observing tube, which is near the ground surface. A case that the water level measuring range is greater often happened.

There were sonic level meters developed to measure a water level, accurately, if the water level measuring range is great. Typical some sonic level measuring method and apparatus having the relatively higher accuracy are disclosed in patents as follows:

U.S. Pat. No. 5,842,374 published on Dec. 1, 1998

Germany Patent No. 19511234 published on Sep. 11, 1997

Japanese Patent No. 2,756,647 published on Mar. 13, 1998

Korean Patent No. 150714 published on Jun. 16, 1998

These patents are commonly entitled as Measuring method of wide range level and apparatus thereof.

A conventional sonic level measuring method previously disclosed is illustrated in FIG. 1. 1 is a sonic generator, 2 is a waveguide tube and $5_1, 5_2, 5_3, \ldots 5_n, 5_{n+1}$ are sonic receivers that are arranged in a constant interval l along the waveguide tube 2. The position of the sonic receiver $5_1$ is an original point or zero point to measure the water level. A distance Lx from the original point to a water surface is measured as follows: as the sonic generator 1 generates sonic pulses, the sonic pulse is transited or propagated toward the water surface, reflected on the water surface and then transited upward. At the moment that the sonic pulses reach the original point, the sonic receiver $5_1$ generates an outputting signal. Similarly, as the sonic pulses are advanced, the sonic receiver $5_n$ nearest to the water surface generates the outputting signal and also receives reflected sonic pulses. Therefore, the water level Lx is subject to being measured using four signals received like this. A time interval $t_1$ between time points that the sonic receiver $5_1$ receives the advancing pulse and the reflected pulse is as follows:

$$t_1 = \frac{2Lx}{c_1} \quad (1)$$

A time interval $t_2$ between time points that the sonic receiver $5_1$ and $5_n$ receive the advancing pulse, respectively, is as follows:

$$t_2 = \frac{L_0}{C_2} = \frac{(n-1)l}{C_2} \quad (2)$$

Wherein, $L_0=(n-1)$ l is a distance that is accurately measured, previously, $L_0$=const, $C_1$ is a sound velocity in the interval Lx, $C_2$ is a sound velocity in the interval $L_0$, and n is the number of the sonic receivers.

A value of Lx to be measured in the expressions (1) and (2) as follows:

$$L_x = \frac{t_1}{2t_2} \times L_0 \times \frac{C_2}{C_1} \quad (3)$$

Wherein, $L_0$ is a previously known value, $t_1$ and $t_2$ and measured and substituted into the expression (3), and $C_1$ and $C_2$ are not known. Assuming that Lx is approximately equal to $L_0$, and $C_1 \approx C_2$, L'x is as follows:

$$L'_x = \frac{t_1}{2t_2} \times L_0 \quad (4)$$

In case that $C_1 \neq C_2$, $Lx \neq L_0$. A measuring error $\delta_{Lx}$ of Lx occurs as follows:

$$\delta_x = \frac{L'_x}{L_x} - 1 = \frac{C_2}{C_1} - 1 \quad (5)$$

When Lx is measured, it is assumed that each of the sound velocity $C_1$ and $C_2$ is changed in the interval's Lx and $L_0$ as follows:

$$C_1 = C_0 + \alpha(\overline{T}_{L_x})$$
$$C_2 = C_0 + \alpha(\overline{T}_{L_G}) \quad (6)$$

Wherein, $\alpha$ is a temperature coefficient of a sound velocity in air, $\alpha \approx 0.6$. $C_0$ is a sound velocity, when an air temperature is zero.

In order to evaluate the error $\delta_{Lx}$ in the patents described above, assuming that the air temperature in the waveguide tube from the original point 0 to the water surface is changed in a straight gradient of $$\frac{T_0 - T_{Lx}}{Lx}$$

as shown in FIG. 2, when $C_1$ and $C_2$ are calculated and then the results are substituted into the error expression (5), the error $\delta_{L'x}$ is as follows:

$$\delta_{L'_x} = \frac{0.5a(T_0 - T_{Lx})}{C_0 + 0.5a(T_0 - T_{Lx})} \times \frac{\Delta L}{L_x}$$

Wherein, $T_0$ is a temperature at the original point and $T_{Lx}$ is a temperature at the water surface.

A maximum error $\delta_{Lxmax}$ appears when $\Delta_{Lmax} \approx 1$.

$$\Delta_{Lxmax} = \frac{0.5a(T_0 - T_{Lx})}{C_0 + 0.5a(T_0 - T_{Lx})} \times l \quad (7)$$

An absolute error $\Delta_{lmax}$ is as follows:

$$\delta_{Lxmax} = \frac{0.5a(T_0 - T_{Lx})}{C_0 + 0.5a(T_0 - T_{Lx})} \times \frac{l}{L_x} \quad (8)$$

If a water level measuring allowance absolute error $\Delta'_{L'x}$ is given, an interval l between the sonic receivers $5_i$ and $5_{i+1}$ is obtained from the expression (8). Assuming that $C_0=331.6$ m and $\alpha=0.6$, the value of l is as follows:

$$l = \Delta'_{L_x} \times \frac{331.6 + 0.3(T_0 + T_{Lx})}{0.3(T_0 - T_{Lx})} \quad (9)$$

Considering that $T_0=40°$ C., $T_{Lx}=25°$ C. in summer, and $T_0=0°$ C., $T_{Lx}=15°$ C. in winter, in order that $\Delta_{Lx}=0.01$ m (1 cm), l is as follow:

l=0.78 m in summer l=0.74 m in winter

If the interval l between sonic receivers is secured to get smaller, the water level measuring absolute error becomes small more and more. Therefore, the conventional sonic level measuring method has great advantages in that the water level absolute error $\Delta_{L'x}$ is equal throughout a full range to measure the water level independent of the water level measuring range and can be secured to be smaller.

The sonic level measuring method has another method as follows: it saves the mounting cost by which the waveguide tube can be mounted along a gradient surface of a river bank and a reservoir bank unlike other sonic level meters. In this case, a length of the waveguide tube is the multiplication of a value Lx measured by the sonic level meter and sin=45°, and a water level changing range of a reservoir is 50 m, the length of the wave guide tube must be over 70.7 m by 50 m/sin45°.

But, the conventional sonic level measuring method has problems as follows: in case that $T_0$ and $T_{Lx}$ in the expression (9) are often changed, and the absolute allowance error $\Delta'_{L'x}=\pm 0.001$ m, l=0.74–0.78 m must be secured. If it is necessary to measure the water level of a reservoir, more accurately, l=0.37–0.39 m must be secured, so that $\Delta'_{L'x}=\pm 0.0005$ m. In this case, if the maximum water level measuring range is 70 m, the number of the sonic receivers is as follows:

$$n \approx \frac{70m}{0.37m} = 189 \approx 190$$

Even if $\Delta'_{L'x}=\pm 0.01$ m is secured, $n \approx 85$ is required. In case that a large number of the sonic receivers are mounted along the lengthwise portion of the waveguide tube, a water level measuring apparatus becomes complex, and also the failure possibility of the sonic receivers may be heightened. Furthermore, another problem happens as follows: a time interval $t_1=2$ Lx/$C_1$ between an advancing wave and a reflected wave must be measured [referring to the expression (1)]. As Lx becomes longer, the sonic pulse is largely reduced during being transited through the distance 2 Lx. For it, a relatively stronger sonic pulse should be emitted, so a reverberation time becomes longer thereby to increase a noise level. In order to prevent these phenomena, the intensity of the sonic pulse should be adjusted based on the change of the measuring value Lx, but it makes a level meter get complex. An object of the invention is to provide a sonic level measuring method for increasing a water level measuring range by approximate two times as long as a prior art, by which even through an interval l between sonic receivers is selected to be far longer than that in the prior art, a water level measuring error is not increased, and receiving the sonic pulse that is reflected on a water surface and then returned to an original point is not required.

SUMMARY OF THE INVENTION

According to the invention, a sonic level measuring method comprises steps of disposing a plurality of N sonic receivers at a constant interval l toward a water surface along the longitudinal portion of a waveguide tube, oscillating sonic pulses to detect the number $N_i$ of the sonic receivers and computing an interval $L_i=(N_i-1)l$ between a sonic receiver $5_i$ disposed nearest the water surface and first sonic receiver $5_1$ that is positioned on the original point for the water level measurement, measuring a transit time $$t_1 = \frac{l}{C}$$

that it takes for the sonic pulse to be transited between a sonic receiver $5_{i-1}$ and the sonic receiver $5_i$, measuring a transit time $$t_2 = \frac{2\Delta L}{C}$$

from the receiving moment of the advancing sonic pulse until the sonic pulses are reflected on the water surface and then again received by the sonic receiver $5_i$, computing an interval $\Delta L$ between the sonic receiver $5_i$ and the water surface, adding the interval $\Delta L$ to $L_1$ and obtaining a distance $Lx=L_i+\Delta L$ thereby to measure the water level.

BRIEF DESCRIPTION OF THE DRAWINGS

The invention will be now just described in detail in reference to the accompanying drawings in which:

FIG. 1 is a view illustrating the sonic level measuring principle according to a prior art;

FIG. 2 is a view illustrating the air temperature distribution in a waveguide tube of a sonic level meter;

DETAILED DESCRIPTION OF THE INVENTION

Figure 3:
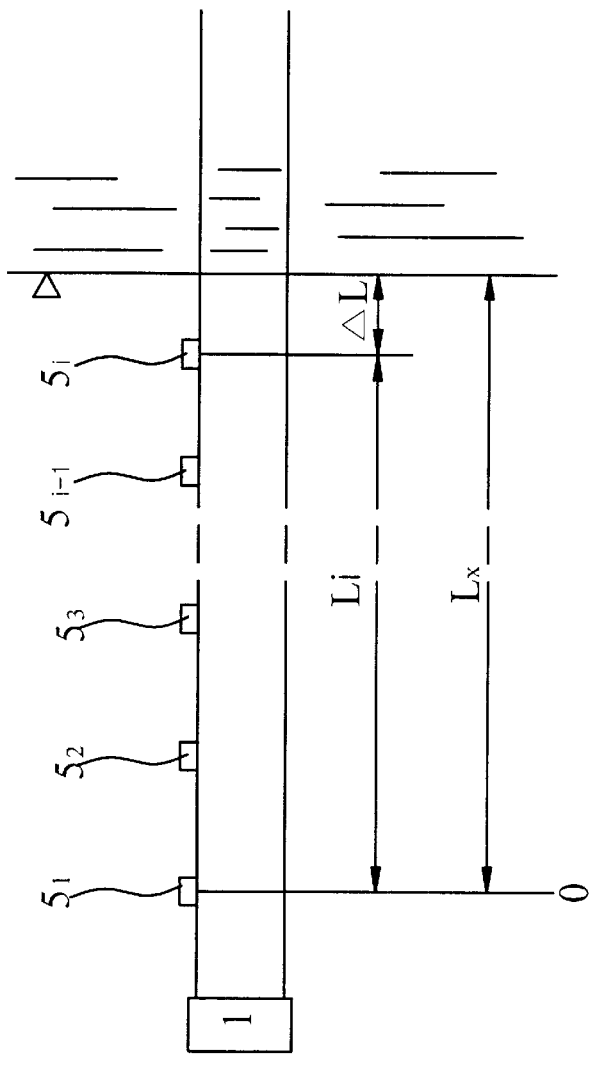
FIG. 3 is a view illustrating the sonic level measuring principle according to the invention.
Figure 4:
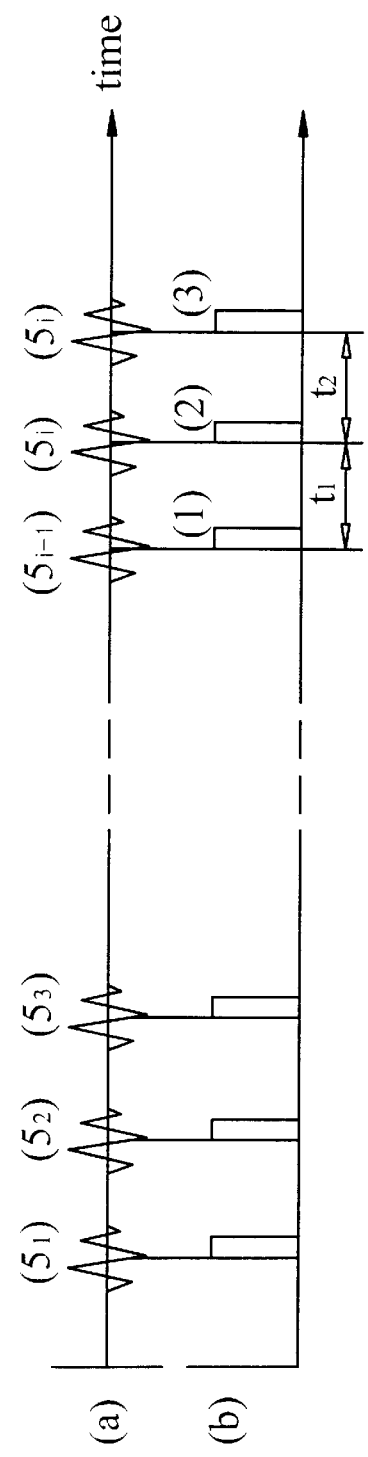
FIGS. 4A and 4B are views illustrating a waveform and a time sequence among sonic receivers according to the invention; and, FIG. 5 is a view illustrating the air temperature distribution in a waveguide tube of a sonic level meter according to the invention.

The invention will be explained referring to FIGS. 3 and 4 as below. A waveguide tube 2 is drawn in a horizontal state for the purpose of easily having the invention understood. When a sonic generator 1 generates sonic pulses, the sonic pulses are transited toward the water surface along a waveguide tube 2. Sonic receivers $5_1$, $5_2$, $5_3$, $5_l$ sonic pulses transited and output a signal representing the receiving of the sonic pulse in turns. Therefore, the number of the sonic receivers that receive the receive sonic pulse is confirmed. A distance $L_i$ from the sonic receiver $5_1$ to $5_i$ is calculated as follows:

$$L_i = (N_i - 1)l \tag{10}$$

Also, if the distance $L_i$ from the sonic receiver $5_1$ to $5_i$ was previously measured and stored at a memory of a system, the calculation of the distance $L_i$ is not required without the expression(10). In other words, a distance $L_2$ from the sonic receivers $5_1$ to $5_2$ a distance $L_3$ from the sonic receiver $5_1$ to $5_3$ . . . a distance $L_{i-1}$ etc., are previously measured to be stored at a level Arithmetic Logic Processing System. It is preferable that l=const. is stored at a level computing system. A distance Lx to be measured is obtained by the measuring an interval $\Delta L$ from the position of the sonic receiver $5_i$ to a water surface and adding it to a distance $L_i$, which is represented as follows:

$$Lx = L_i + \Delta L \tag{11}$$

A measuring method will be explained below referring to FIG. 4. As shown in FIG. 4A, the sonic receivers $5_1$, $5_2$, $5_3$ . . . $5_i$ generate the outputting signals upon receiving advancing pulses. Thereafter, the sonic receiver $5_i$ again generates the outputting signal which represents the receipt of the sonic pulse reflected on the water surface. And, the outputting signals are applied in turns to a zero-crossing detecting circuit and a waveform shaping circuit, so that square pulses (1),(2),(3) are generated in turns as shown in FIG. 4B. At this time, time intervals $t_1$ between the pulses (1) and (2) and $t_2$ between the pulses (2) and (3) are as follows:

$$t_1 = \frac{l}{C_l} \tag{12}$$

$$t_2 = \frac{2\Delta L}{C_{\Delta L}} \tag{13}$$

The $t_1$ of the expression (12) also can be measured in a manner that a time $t_{1,4}$ that it takes for a sonic receiver $5_{i-1}$ to receive the advancing pulse and then the pulse reflected on the water surface is measured and the time $t_2$ is subtracted therefrom(referring to FIG. 4B), which is represented as follows:

$$\Delta t = t_{1,4} - t_2 = \frac{2(l + \Delta L)}{C_{1,4}} - \frac{2\Delta L}{C_{\Delta L}} = \frac{2l}{C_l} \tag{14}$$

An unknown value $\Delta L$ in the expressions (12) and (13) is calculated as follows:

$$\Delta L = \frac{t_2}{2t_1} \times l \times \frac{C_{\Delta L}}{C_l} \tag{15}$$

On the other hand, $\Delta L$ is calculated using the expressions (14) and (12) as follows:

$$\frac{t_2}{\Delta t} = \frac{t_2}{t_{1,4} - t_2} = \frac{2\Delta L C_l}{2l C_{\Delta L}} \tag{16}$$

$$\therefore \Delta L = \frac{t_2}{t_{1,4} - t_2} \times l \times \frac{C_{\Delta L}}{C_l}$$

Herein, the difference between the expressions (15) and (16) is as follows: if $\Delta L$ is measured according to the expression (16), it has an advantage in that thanks to a term $\Delta t = t_{1,4} - t_2$ the measuring fixing errors of the transit times $t_{1,4}$ and $t_2$ are compensated for each other, but an accidental error of the expression (16) is equal to $\delta_{t1,4} + 2\delta_{t2}$. Therefore, if the fixing error of the transit time measuring is small enough to be ignored, it is a better exact thing to measure the $\Delta L$ based on the expression (15). Under the condition that sound velocities $C_{\Delta L}$ and $C_l$ are unknown, assume that $C_{\Delta L} = C_l$, $\Delta L'$ is measured as follows:

$$\Delta L' = \frac{t_2}{2t_1} \times l \tag{17}$$

or $$\Delta L' = \frac{t_2}{t_{1,4} - t_2} \times l \tag{18}$$

Therefore, if the transit time measuring error is ignored, the error $\delta_{\Delta L}$, is as follows:

$$\delta_{\Delta L'} = \frac{C_l}{C_{\Delta L}} - 1 \tag{19}$$

Figure 5:
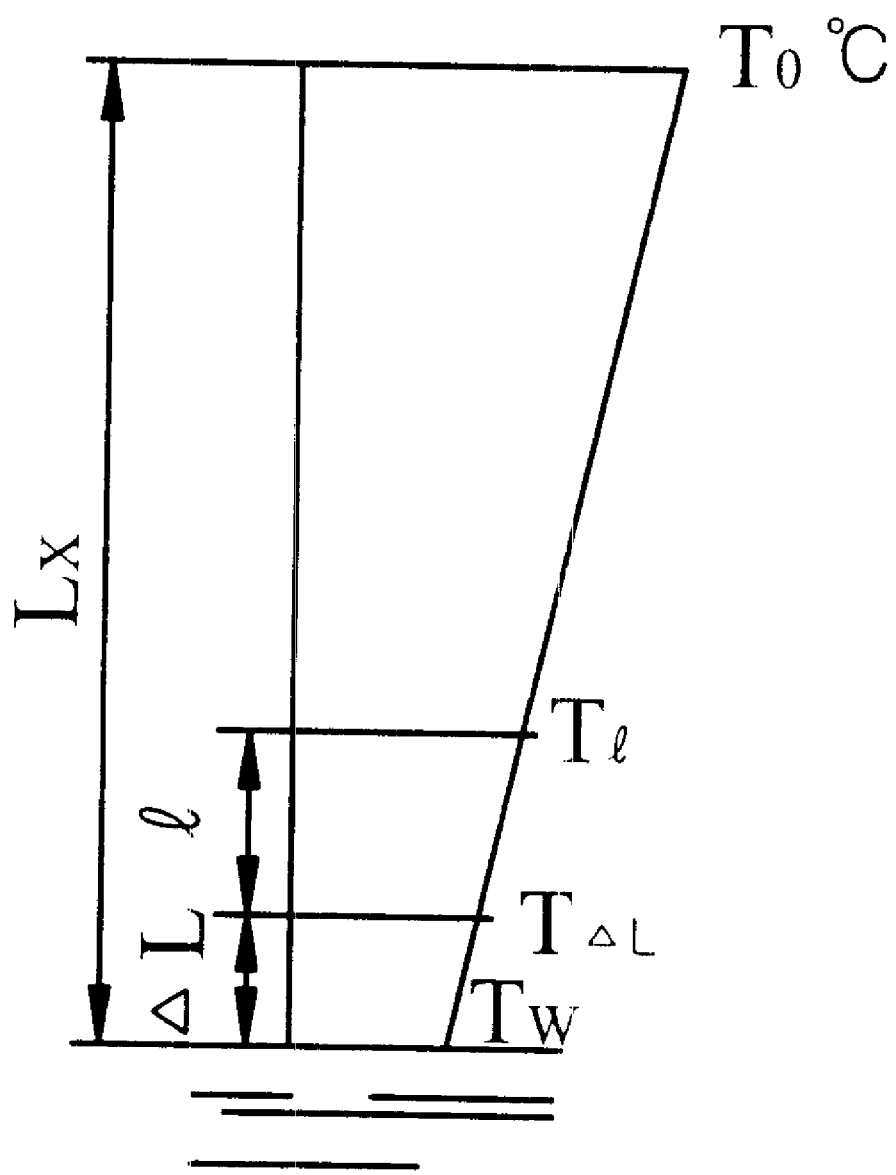

The error $\Delta L'$ measured by the method described above is represented under the condition that is equal to that for evaluating an error according to a prior art referring to FIG. 5 as follows:

FIG. 5 shows the change of air temperature distributed along the length in a waveguide tube 1. A temperature $T_l$ at a point that a sonic receiver $5_{i-1}$ is disposed and a temperature $T_{\Delta L}$ at a point that a sonic receiver $5_1$ is disposed are as follows: a temperature at an original point that a sonic receiver $5_i$ is disposed is represented as $T_0$ and a temperature at a water surface is as $T_w$.

$$T_l = T_w + (T_0 + T_w)\frac{l + \Delta L}{L_x} = T_w + \Delta T \frac{l + \Delta L}{L_x}$$

$$T_{\Delta L} = T_w + \Delta T \frac{\Delta L}{L_x}$$

Wherein, $\Delta T = T_0 - T_w$ is a temperature difference an upper portion and a water surface in the waveguide tube.

An average temperature $\overline{T}_l$ in the interval l and an average temperature $\overline{T}_{\Delta L}$ in the interval $\Delta L$ are as follows:

$$\overline{T}_l = \frac{T_1 + T_{\Delta L}}{2} = \frac{T_w + \Delta T \frac{l + \Delta L}{L_x} + T_w + \Delta T \frac{\Delta L}{L_x}}{2} \tag{a}$$

$$= T_w + \frac{\Delta T}{2L_x}(l + \Delta L)$$

$$\overline{T}_{\Delta L} = \frac{T_{\Delta L} + T_w}{2} = \frac{T_w + \Delta T \frac{\Delta L}{L_x} + T_w}{2} = T_w + \Delta T \frac{\Delta L}{2L_x} \tag{b}$$

Substitution of the expressions (a) and (b) into the sound velocity expression (6) is as follows:

$$C_l = C_0 + \alpha \overline{T}_l = C_0 \left[1 + \beta\left(T_w + \Delta T \frac{l + \Delta L}{2L_x}\right)\right] \tag{c}$$

-continued $$C_{\Delta L} = C_0 + \alpha \overline{T}_{\Delta L} = C_0\left[1 + \beta\left(T_w + \Delta T \frac{\Delta L}{2L_x}\right)\right] \quad (d)$$

Wherein, $$\beta = \frac{\alpha}{C_0} \approx \frac{0.6}{331.6} = 1.8 \times 10^{-3}.$$

Considering that β

$$\beta\left(T_w + \Delta T \frac{\Delta L}{2L_x}\right) \langle\langle 1.0,$$

1.0, a ratio of $$\frac{C_l}{C_{\Delta L}}$$

is obtained as follows:

$$\frac{C_l}{C_{\Delta L}} = \frac{C_0\left[1 + \beta\left(T_w + \Delta T \frac{l + \Delta L}{2L_x}\right)\right]}{C_0 + \left[1 + \beta\left(T_w + \Delta T \frac{\Delta L}{2L_x}\right)\right]} \quad (20)$$

$$\approx \left[1 + \beta\left(T_w + \Delta T \frac{l + \Delta L}{2L_x}\right)\right]\left[1 - \beta\left(T_w + \Delta T \frac{\Delta L}{2L_x}\right)\right]$$

$$= 1 + \beta\left[T_w + \Delta T \frac{l + \Delta L}{2L_x} - T_w - \Delta T \frac{\Delta L}{2L_x}\right]$$

$$\approx 1 + \beta \frac{\Delta T}{2L_x} \times l$$

$$\therefore \delta_{\Delta L'} = \frac{C_l}{C_{\Delta L}} - 1 \approx \beta \frac{\Delta T}{2L_x} \times l$$

Wherein, because a term $-\beta^2[T_w + \Delta T \times$ $$\text{term} - \beta^2\left[T_w + \Delta T \times \frac{\Delta L}{2Lx}\right]^2$$

is ignored, $\delta_{\Delta L}$, is represented to have a larger value.

The measuring absolute error $\Delta_{\Delta L}$ of $\Delta L$ is as follows:

$$\Delta_{\Delta L} = \delta_{\Delta L} \times \Delta L = \beta \frac{\Delta T}{2L_x} \times l \times \Delta L \quad (21)$$

If $\Delta L \approx 1$, $\Delta_{\Delta L}$ gets maximized $$\Delta_{\Delta L \max} = \beta \frac{\Delta T}{2L_x} \times l^2 = 1.8 \times 10^{-3} \frac{T_0 + T_w}{2L_x} \times l^2 \quad (22)$$

A total absolute error of Lx according to the level measuring is as follows:

$$\Delta_{L_x} = \Delta_{L_l} + \Delta_{\Delta L} \quad (23)$$

And, a relative error $\delta_{Lx}$ is as follows:

$$\delta_{L_x} = \frac{\Delta L_i}{L_x} + \frac{\Delta_{\Delta L}}{L_x} \quad (24)$$

The distance $L_l$ from the original level measuring original point to the position of the sonic receivers $5_i$ is a constant which is exactly measured by a precise distance measuring device and then stored at the level computing system. For it, its error $\Delta_{Li}$ and $\delta_{Ll}$ can be secured to become small enough to be disregarded. Considering level measuring allowance absolute errors as $\Delta_{\Delta L}$ and $\Delta_{\Delta Lmax}$, a required value l is obtained as follows:

$$l = \sqrt{\frac{2\Delta_{\Delta L} \times L_x}{1.8 \times 10^{-3}(T_0 - T_w)}} = \sqrt{\frac{1.11 \times \Delta_{\Delta L} \times L_x \times 10^3}{T_0 - T_w}} \quad (25)$$

On the other hand, under the condition of the prior art the l is obtained as follows; assuming that Lx=70 m, $T_0$=40°, Tw=25° and $\Delta_{\Delta L}$=0.005 m (5 mm), the value is substituted into the expression (22) as follows:

$$l = \sqrt{\frac{1.11 \times 0.005 \times 70 \times 10^3}{40 - 25}} = 5.09 \approx 5m$$

With it, the prior art must be secured so that l=0.37. On the contrary, according to the invention the l is extended 5 m/0.37=13.5 times as long as the prior art. Therefore, the number of the sonic receivers to be mounted in the waveguide tube having a length of Lx=70 m is 14 that is equal to 70/5. According to the prior art, the sonic receivers of N=190 were required. Herein, it is noted that as the level measuring range Lx becomes larger in the expressions (21) and (22), the measuring error of ΔL is reduced.

Therefore, the invention has specific features as follows: unlike the prior art, the sonic receiver $5_1$ need not receive a sonic pulse that is reflected on the water surface and returned to the original point. Therefore, if a sonic generator that is the same as that of the prior art is used, the measuring range is increased approximately two times as long as a conventional method.

As a result, the invention secures the accuracy of the level measurement compared with the conventional sonic level measuring method, decreases the number of the sonic receivers over tem times and increase the measuring range over two times.

What is claimed is:

1. A sonic level measuring method including steps of disposing a plurality of N sonic receivers at a constant interval l toward a water surface along the longitudinal portion of a waveguide tube, constituting a position of first sonic receiver as an original point of the water level measurement and emitting sonic pulses from the upper portion of a waveguide tube to measure a distance Lx from the original point to the water surface, comprising steps of:

measuring a transit time $t_1$ that it takes for advancing sonic pulses to be transited between two sonic receivers nearest to the water surface;

measuring a transit time $t_2$ from the receiving moment of the advancing pulse until the sonic pulse is reflected on the water surface and again received by the sonic receiver nearest to the water surface;

computing an interval ΔL between the sonic receiver nearest the water surface to the water surface by the following expression;

$$\Delta L = \frac{t_1}{2t_2} \times l$$

computing a distance $L_l$ from the original point till the sonic receiver disposed nearest to the water surface by the following expression; and $$L_l = (N_l - 1)l$$

adding the interval $\Delta L$ to the distance $L_l$ thereby to computing Lx.

wherein, $N_l$ is the number of sonic receivers including the sonic receiver at the original point the sonic receiver nearest to the water surface, l is an interval between the sonic receivers.

2. The sonic level measuring method as claimed in claim 1, in which:

the interval l between the sonic receivers is selected based on the following expression.

$$l = \sqrt{\frac{1.11 \times \Delta_{\Delta L} \times L_x \times 10^3}{T_0 - T_w}}$$

wherein, $\Delta'_{\Delta L}$ is a measuring allowance absolute error of $\Delta L$, Lx is a lever measuring maximum range and $T_0$ and Tw are temperature °C. at the upper portion of the waveguide tube and near the water surface of the waveguide tube that be expected.

\* \* \* \* \*